US009513232B2

(12) United States Patent
Cox et al.

(10) Patent No.: US 9,513,232 B2
(45) Date of Patent: Dec. 6, 2016

(54) METHOD FOR TRIGGERING DEPENDENT SPECTRA FOR DATA ACQUISITION

(75) Inventors: David M. Cox, North York (CA); Stephen A. Tate, Barrie (CA); Matthias Glueckmann, Oberursel (DE)

(73) Assignee: DH Technologies Development Pte. Ltd., Singapore (SG)

( * ) Notice: Subject to any disclaimer, the term of this patent is extended or adjusted under 35 U.S.C. 154(b) by 629 days.

(21) Appl. No.: 13/995,816

(22) PCT Filed: Dec. 22, 2011

(86) PCT No.: PCT/IB2011/003107
§ 371 (c)(1),
(2), (4) Date: Jun. 19, 2013

(87) PCT Pub. No.: WO2012/090046
PCT Pub. Date: Jul. 5, 2012

(65) Prior Publication Data
US 2013/0289894 A1    Oct. 31, 2013

Related U.S. Application Data

(60) Provisional application No. 61/427,860, filed on Dec. 29, 2010.

(51) Int. Cl.
*H01J 49/00*   (2006.01)
*G01N 23/00*   (2006.01)
*H01J 49/02*   (2006.01)

(52) U.S. Cl.
CPC ........... *G01N 23/00* (2013.01); *H01J 49/0031* (2013.01); *H01J 49/0045* (2013.01); *H01J 49/025* (2013.01)

(58) Field of Classification Search
CPC ..... G01N 23/00; H01J 49/025; H01J 49/0045; H01J 49/0031
(Continued)

(56) References Cited

U.S. PATENT DOCUMENTS

2001/0052569 A1* 12/2001 Bateman ............. H01J 49/4215
250/288
2006/0284069 A1* 12/2006 Le Blanc ............ H01J 49/0036
250/282

(Continued)

FOREIGN PATENT DOCUMENTS

WO    2009127808 A2    10/2009

*Primary Examiner* — Michael Maskell
(74) *Attorney, Agent, or Firm* — John R. Kasha; Kelly L. Kasha; Kasha Law LLC (57) ABSTRACT

Methods and systems are provided for triggering an information dependent mass spectrometry scan in real time. A mass spectrometry scan of a separating sample mixture is performed by a mass spectrometer at each time interval of a time period. The mass spectrometer receives the separating sample mixture from a separation device. It is determined at a certain time interval that a received mass spectrometry scan at the time interval and one or more preceding received mass spectrometry scans include two or more time-varying ion signals that represent two or more fragment ion transitions of a known compound. If a characteristic of the two or more time-varying ion signals meets a selection criterion, the mass spectrometer is instructed to perform a dependent mass spectrometry scan of the separating sample mixture for a precursor ion of the known compound at the time interval.

20 Claims, 7 Drawing Sheets (58) Field of Classification Search
USPC .................................. 250/281, 282, 287, 288
See application file for complete search history.

(56) References Cited

U.S. PATENT DOCUMENTS

2010/0276583 A1  11/2010  Senko
2013/0105682 A1* 5/2013  Geromanos ........... H01J 49/005
                                              250/282

* cited by examiner

FIG. 1

(PRIOR ART)

METHOD FOR TRIGGERING DEPENDENT SPECTRA FOR DATA ACQUISITION

CROSS-REFERENCE TO RELATED APPLICATION

This application claims the benefit of U.S. Provisional Patent Application No. 61/427,860 filed Dec. 29, 2010, which is incorporated by reference herein in its entirety.

INTRODUCTION

Mass spectrometers are often coupled with chromatography systems in order to identify and characterize eluting species from a test sample. In such a coupled system, the eluting solvent is ionized and a series of mass spectral images are obtained of the eluting solvent at specified time intervals producing a mass spectrogram. These time intervals range from, for example, 1 second to 100 minutes or greater. As the test sample may contain many species or compounds, it is often desirable to be able to automatically determine or identify species or compounds of interest as they elute and perform tandem mass spectrometry, or mass spectrometry/mass spectrometry (MS/MS), analysis to characterize them. However, identifying species of interest in complex mixtures in real time can be a challenging task.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
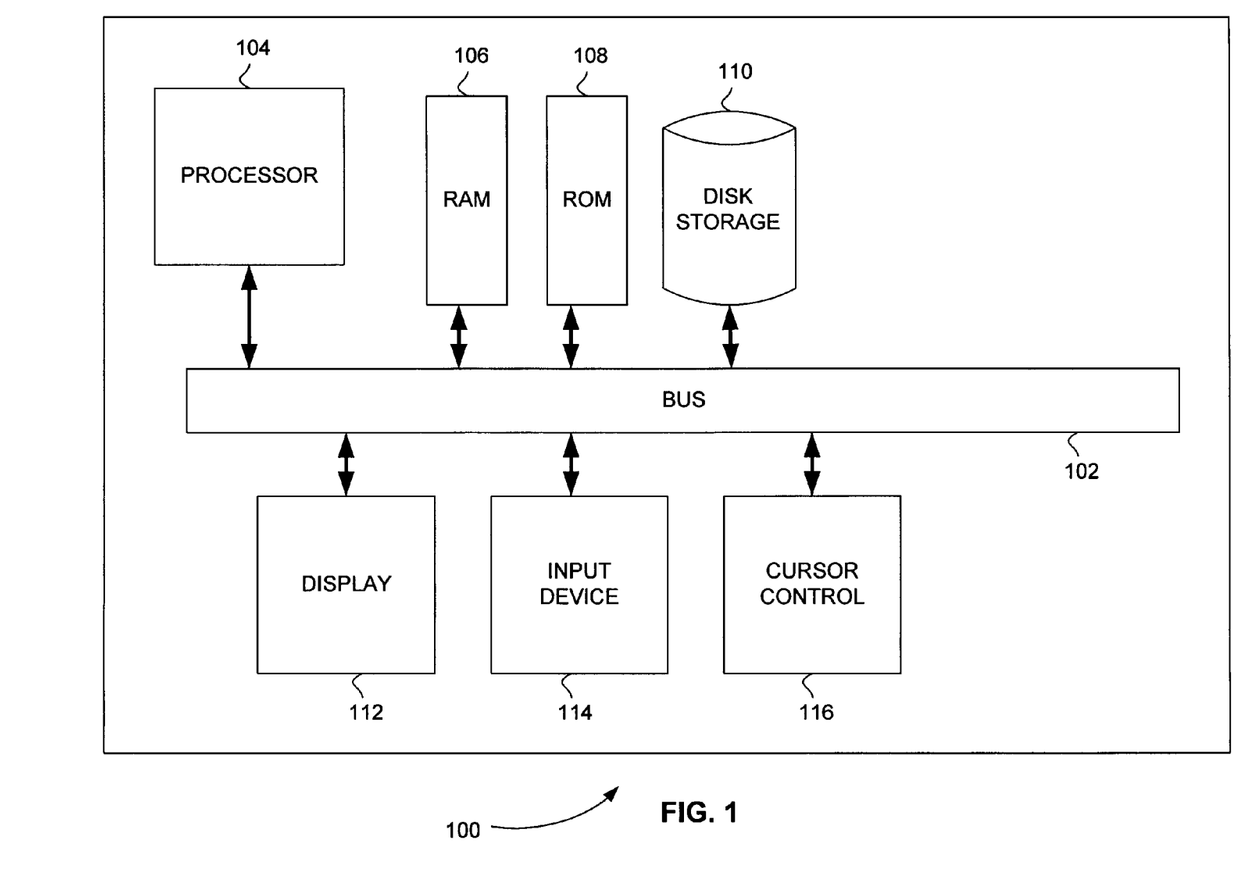
FIG. 1 is a block diagram that illustrates a computer system, in accordance with various embodiments.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Identifying Separated Compounds

Various embodiments include systems and methods for identifying separated compounds in a separation device/mass spectrometry system. One or more dependent mass spectrometry scans are triggered based on characteristics of a group of two or more mass spectrometry/mass spectrometry (MS/MS) transition targets found in a time-varying image from the separation device. In various embodiments, data acquisition and analysis software associated with the mass spectrometer and the separation devices is used to achieve this goal.

Exemplary and well-known data acquisition and analysis software includes the information dependent acquisition (IDA) system marketed by AB Sciex. During the data acquisition process this software identifies a mass peak in a mass spectrogram so as to select a precursor ion. The software then directs one or more subsequent stages of mass spectrometry such as MS/MS, mass spectrometry/mass spectrometry/mass spectrometry (MS/MS/MS), or any higher order stage mass spectrometry ($MS^n$, where n is integer), in which the chosen precursor ion is fragmented. The resulting MS/MS (or higher) spectrum is a composite of all the fragmentation processes that are energetically allowed. These processes include precursor ion to fragment ion reactions and fragment ions to other fragment ions reactions.

Software such as IDA is particularly useful for selected reaction monitoring (SRM) or multiple reaction monitoring (MRM) experiments. Such experiments can elucidate the spectral richness and/or the dissociation pathways used to provide structural information used in characterizing compounds or to identify compounds when searching through spectral databases or MS/MS libraries.

Figure 2:
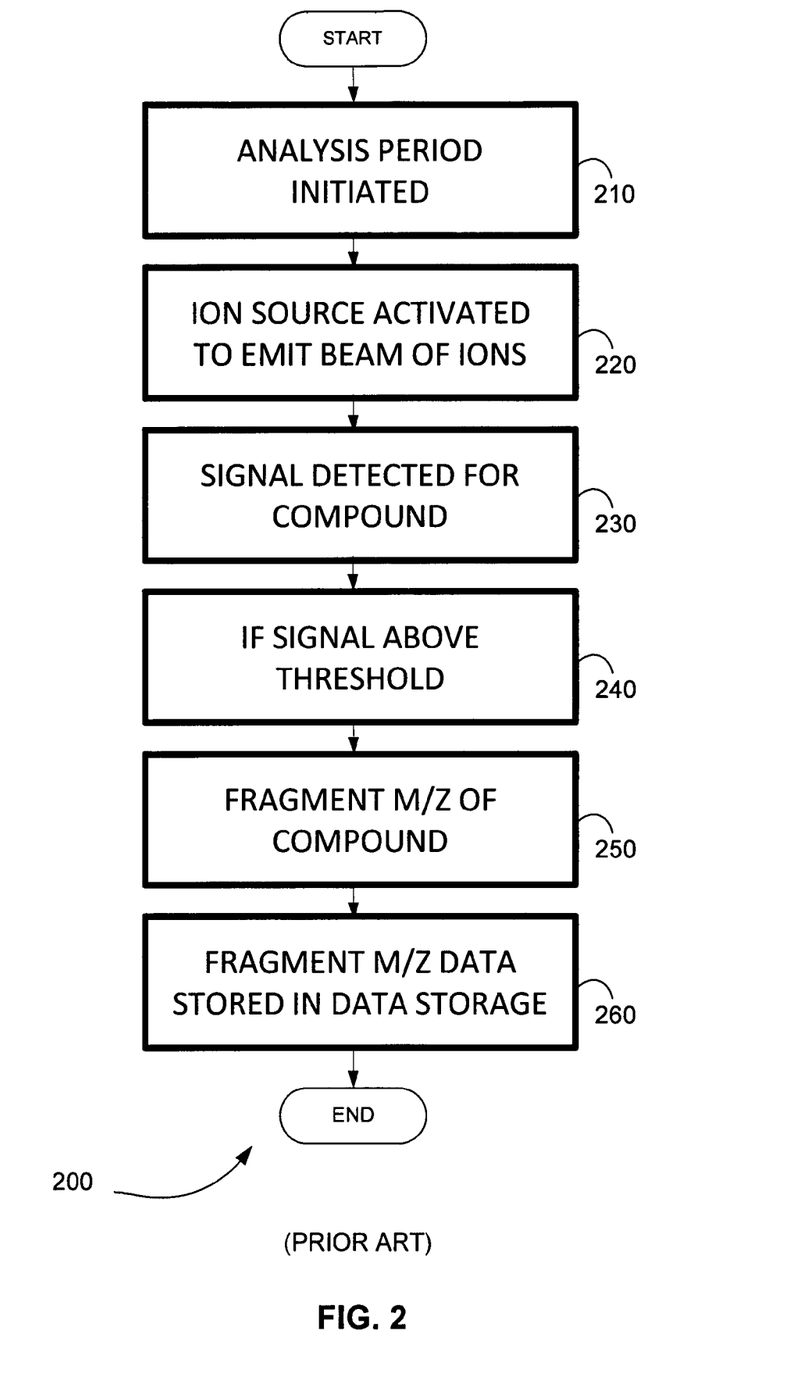
FIG. 2 is an exemplary flowchart showing a selected reaction monitoring (SRM) or multiple reaction monitoring (MRM) method using a conventional information dependent acquisition (IDA) system.

FIG. 2 is an exemplary flowchart showing an SRM or MRM method 200 using a conventional IDA system.

In step 210 of method 200, an analysis period is initiated for a separation device.

In step 220, an ion source is activated to emit a beam of ions.

In step 230, a signal is detected for a compound in a mass spectrogram.

In step 240, it is determined if the signal detected for the compound in the mass spectrogram is above a threshold.

In step 250, if the signal detected for the compound is above a threshold, a dependent scan is performed to fragment the compound, using the mass spectrometer.

In step 260, fragment data from the dependent scan is stored in a memory.

The use of real time data acquisition software, such as IDA, as described above, provides good results in applications such as in-vitro sample analysis or single protein digest analysis, where it is possible to detect a mass peak of interest fairly easily. However, when dealing with a more complex sample set, such as a biological fluid (e.g., urine or plasma extracts) or mixtures of digested proteins (e.g., trypsin digested cell lysate), conventional data acquisition and analysis software falls short. For example, there may be many other major components or species eluting at the same time. These other major components or species often have one or more of the same precursor ion corresponding to the signal of the analyte or species of interest, thus making it difficult to effectively select the (ionized) species of real interest.

The selection of the mass peak "chosen" by a system for MS/MS can be improved by triggering the dependant scan from a list of candidates for precursor ion selection based on individual MRM ion signal characteristics, such as the intensity of the m/z of the fragment ion corresponding to the selected precursor ion. However, MRM experiments are often run with multiple MRM per compound (peptide quantitation, ion ratios in pesticide testing, and others). As a result, since each MRM transition is evaluated individually, it is possible to trigger dependent scans several times for the same compound or to trigger at a time in the separation run where the wrong compound is eluting, such as when the ion ratios of MRM from the same compound are incorrect. In essence, this can lead to extraneous and redundant data making interpretation of the results more complicated.

In various embodiments, by combining together the ion signal characteristics of a related group of two or more MRM transitions, a candidate list can be populated with a single selection criterion that can represent the group of MRM ion signal characteristics. The selection criterion can be based on a property calculated from all of the MRM transitions so that when the dependent scan is triggered, each of the ion signal characteristics representing the group of MRM transitions are met at the same time. Any species eluting with overlapping ion signal characteristics without fulfilling the selection criterion may not trigger a dependent scan, effectively reducing the likelihood of a false positive trigger.

In various embodiments, the group of two or more MRM transitions includes two or more fragment ion, or product ion, transitions and the selection criterion is based on one or more signal characteristics of the two or more fragment ion transitions. A precursor ion can have multiple fragment transition targets. A combination of each of the individual fragment transitions can be used to assign a selection criterion to represent the group of MRM transitions.

In one exemplary embodiment, the one or more signal characteristics of the two or more fragment ion transitions include a minimum intensity level. The selection criteria can be a minimum intensity level that each fragment ion of the two or more fragment ion transitions must exceed in order for a dependent scan to be triggered. The intensity level is, for example, a fragment ion's counts per second.

Consider, for example, a compound of interest, "Compound Z", having predetermined MRM transitions of 475→250 amu; 475→175 amu; and 475→100 amu. A minimum intensity level, of say 1000 counts per second (cps), which may also be set independently for each transition or fragment ion, can be identified as a threshold value corresponding to each of the fragment ions' m/z at 250, 175 and 100 amu. A sample with a mixture containing Compound Z and other compounds co-elute from a separation device and, by means generally known in the present art, ion signals are generated. When candidate ion signals corresponding to each of the target fragment ions mass-to-charge ratios (m/z) at 250, 175 and 100 amu elute at the same elution time, a dependent scan is triggered provided that each of the detected ion signals has an intensity level above the threshold value. In addition to intensity, the ion signals can also be analyzed based on other signal characteristics or parameters, including but not limited to, area, shape of the signal, or any other mathematical treatment such as calculating the first derivative of the signal.

Figure 3:
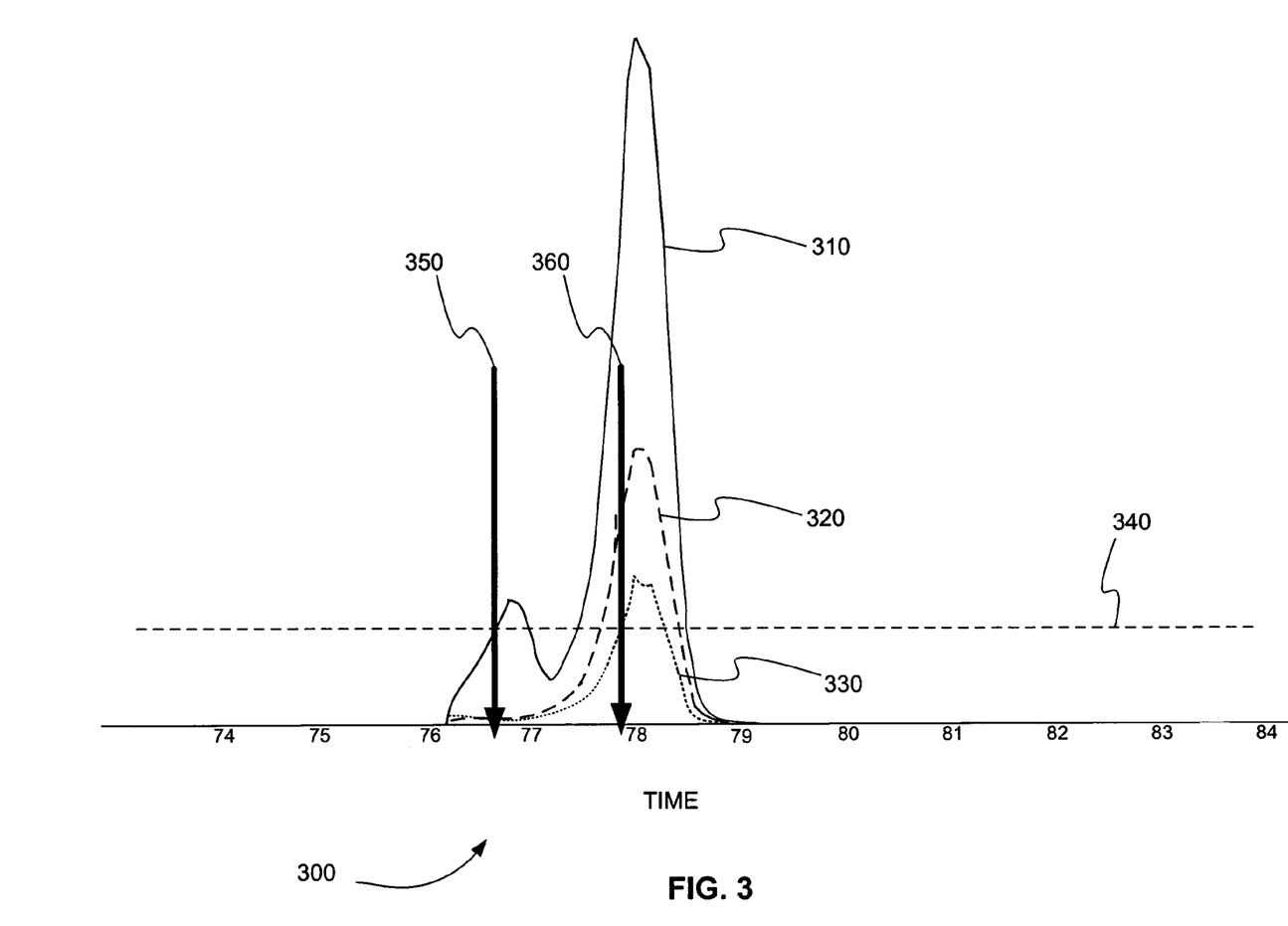
FIG. 3 is an exemplary plot of ion signals of three fragment ions detected in a mass spectrogram and shows where in time a dependent mass spectrometry scan is triggered, in accordance with various embodiments.

FIG. 3 is an exemplary plot 300 of ion signals of three fragment ions detected in a mass spectrogram and shows where in time a dependent mass spectrometry scan is triggered, in accordance with various embodiments. Plot 300 shows ion signal 310 of a first fragment ion, ion signal 320 of a second fragment ion, and ion signal 330 of a third fragment ion. Plot 300 also shows an intensity threshold value 340. As described above, in one exemplary embodiment a dependent mass spectrometry scan is triggered if each fragment ion of two or more fragment ion transitions exceeds a minimum intensity threshold value. As shown in plot 300, threshold value 340 is a minimum intensity threshold value. At time 350, ion signal 310 of the first fragment ion exceeds threshold value 340. However, ion signal 320 of the second fragment ion and ion signal 330 of the third fragment ion do not exceed threshold value 340, so a dependent mass spectrometry scan is not triggered at time 350. In contrast, at time 360 all three ion signals exceed threshold value 340. As a result, a dependent mass spectrometry scan is triggered at time 360, according to this embodiment.

In another exemplary embodiment, the one or more signal characteristics of the two or more fragment ion transitions include a rate at which the ion intensity increases. The rate at which the ion intensity increases for each of the MRM transition targets in a group can be predetermined for use as single selection criteria for each eluting corresponding ion signal. Specifically, when two or more ion signal candidates are detected from a separation as the transition target, a dependent scan is triggered if the rate of the signal increase for each of the two or more ion signal candidates agrees with the predetermined rate at the same transition time. Thus, since each ion signal candidate is subjected to the same rate increase criterion, false triggering of a dependent scan is minimized.

In another exemplary embodiment, the one or more signal characteristics of the two or more fragment ion transitions include a sum of the intensities of the ion signals from the two or more fragment ion transitions. The selection criterion is, for example, a sum of separating ion intensities of separating ion signals that equates to or exceeds a predetermined value. As the group of targeted ion signals is detected, the intensity of each MRM transition is added and compared to an expected or predetermined total value. A dependent scan is triggered if the summation comparison is equal to or greater than the predetermined total value.

In another exemplary embodiment, the one or more signal characteristics of the two or more fragment ion transitions include nonzero the intensity counts of the ion signals from the two or more fragment ion transitions. For example, a multiplication factor based on the MRM transition can be used to identify nonzero targeted candidate ion intensities. As a sample separates, with or without subjecting the ion signal to threshold criteria as above, the intensity of each candidate is multiplied together. If any MRM candidate ion has a zero count value, the separating compound does not trigger a dependent scan. Once the entire group of MRM targets has nonzero signals, then a dependent scan is triggered.

The embodiments have been described with reference to scans that monitor a group of multiple reactions and the selection criteria based on the targeted transitions of these reaction. It is understood, however, that various embodiments can be applied to a wide variety of further selection criteria that can add additional dimensions to reducing a false positive triggering of targeted compounds, including, for example, taking an average of the candidate intensities or other statistical functions of the candidate intensities assigned to the group of related MRM transitions (e.g. the first derivative). It is also understood that the various embodiments can be applied to capillary electrophoresis mass spectrometry systems (CE-MS), chromatography mass spectrometry systems, including gas and liquid chromatography (GC-MS and LC-MS), mobility mass spectrometry systems, and other ion source or separation mass spectrometry combinations not mentioned here. Those skilled in the art will appreciate that a variety of modifications can be made to the preferred embodiments without departing from the spirit of the invention.

Figure 4:
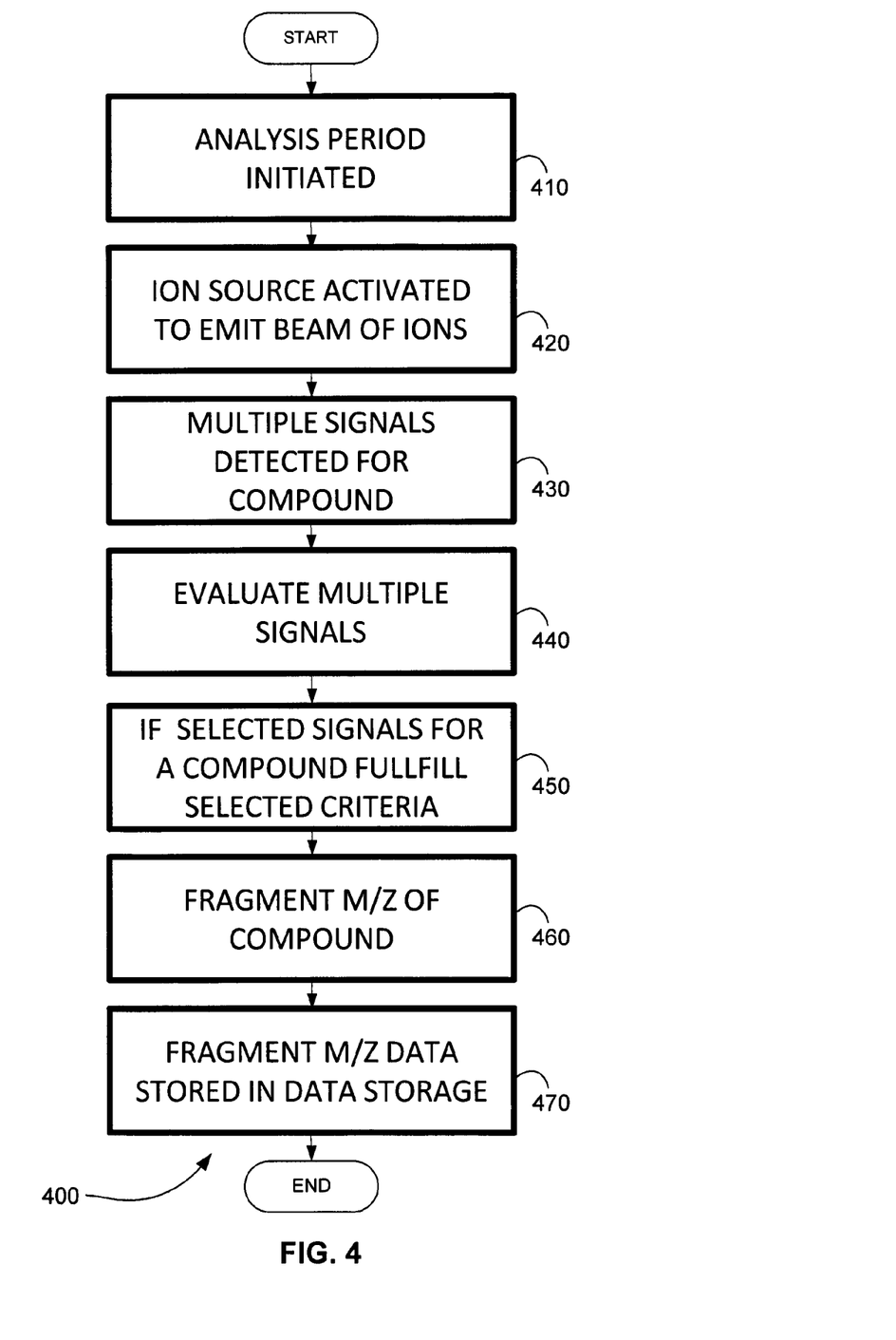
FIG. 4 is an exemplary flowchart showing an SRM or MRM method using an IDA system, in accordance with various embodiments.

FIG. 4 is an exemplary flowchart showing an SRM or MRM method 400 using an IDA system, in accordance with various embodiments.

In step 410 of method 400, an analysis period is initiated for a separation device.

In step 420, an ion source is activated to emit a beam of ions.

In step 430, two or more signals are detected for a compound in a mass spectrogram.

In step 440, the two or more signals are evaluated based on a selection criterion.

In step 450, it is determined if the two or more signals fulfill the selection criterion.

In step 460, if the two or more signals fulfill the selection criterion, a dependent scan is performed to fragment the compound using the mass spectrometer.

In step 470, fragment data from the dependent scan is stored in a memory.

Systems and Methods of Data Processing

Separation Coupled Mass Spectrometry System

Figure 5:
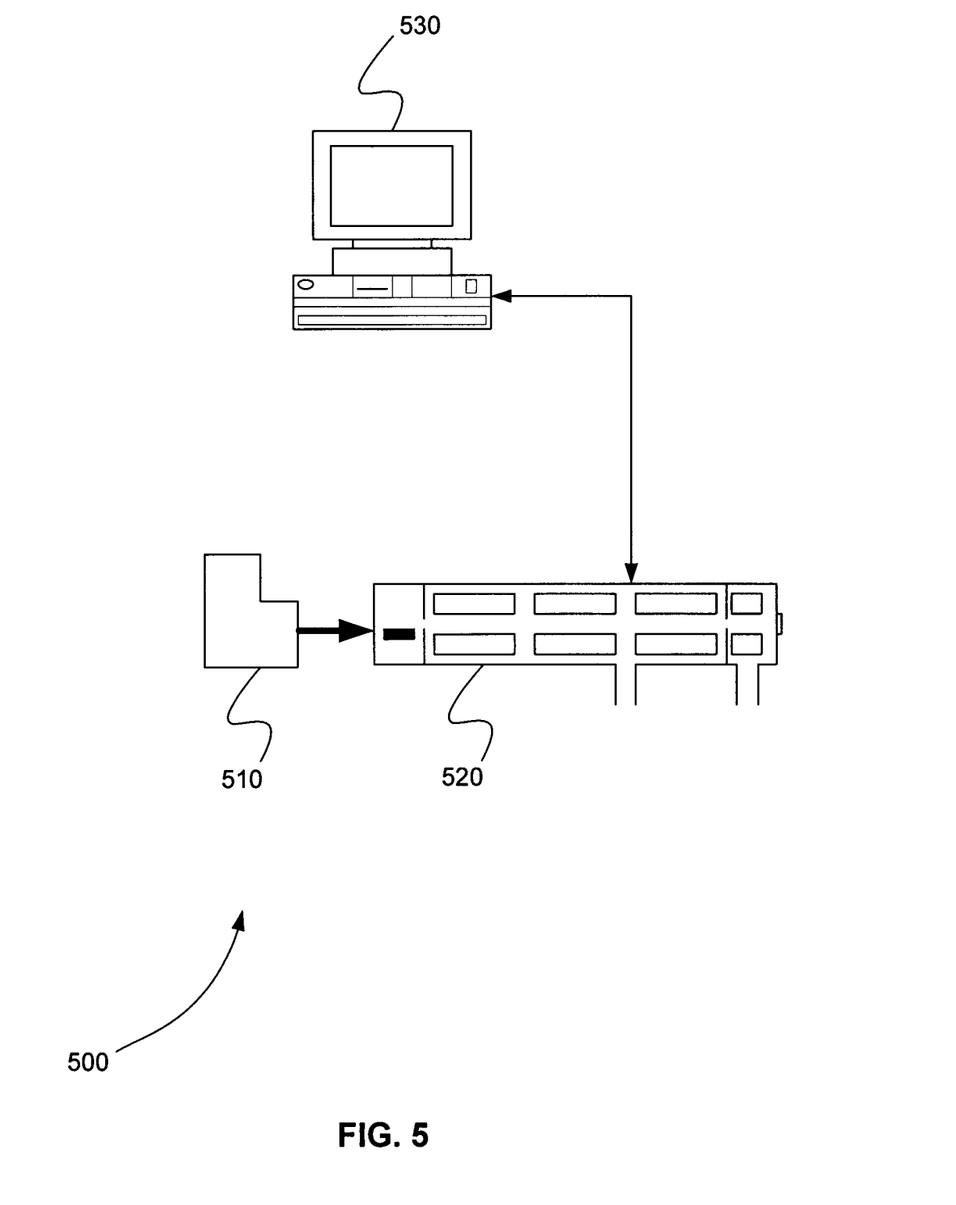
FIG. 5 is a schematic diagram showing a separation coupled mass spectrometry system for triggering an information dependent mass spectrometry scan in real time, in accordance with various embodiments.

FIG. 5 is a schematic diagram showing a separation coupled mass spectrometry system 500 for triggering an information dependent mass spectrometry scan in real time, in accordance with various embodiments. System 500 includes separation device 510, mass spectrometer 520, and processor 530. Separation device 510 separates one or more compounds from a sample mixture over a time period. Separation device 510 can include, but is not limited to, an electrophoretic device, a chromatographic device, or a mobility device.

Mass spectrometer 520 performs a mass spectrometry scan on the separating sample mixture from separation device 510 at a plurality of time intervals of the time period. Mass spectrometer 520 can include one or more physical mass analyzers that perform two or more mass analyses. Mass spectrometer 520 is a tandem mass spectrometer, for example. A mass analyzer of mass spectrometer 520 can include, but is not limited to, a time-of-flight (TOF), quadrupole, an ion trap, a linear ion trap, an orbitrap, a magnetic four-sector mass analyzer, a hybrid quadrupole time-of-flight (Q-TOF) mass analyzer, or a Fourier transform mass analyzer. Mass spectrometer 520 can include separate mass spectrometry stages or steps in space or time, respectively.

Processor 530 is in communication with mass spectrometer 520. Processor 530 can also be in communication with separation device 510. Processor 530 can be, but is not limited to, a computer, microprocessor, or any device capable of sending and receiving control signals and data to and from mass spectrometer 520 and processing data.

Processor 530 receives from mass spectrometer 520 each mass spectrometry scan at each time interval of the plurality of time intervals. As a result, a mass spectrogram can be created piecewise in real time as the sample mixture is separating.

Processor 530 determines at a certain time interval of the plurality of time intervals that a received mass spectrometry scan at the time interval and one or more preceding received mass spectrometry scans include two or more time-varying ion signals that represent two or more fragment ion transitions of a known compound. In other words, time-varying signals can be determined from the current scan and one or more previous scans at each time interval. These signals represent the two or more fragment ion transitions of the known compound if the m/z values of the signals match the m/z values of the two or more fragment ion transitions, for example.

If a characteristic of the two or more time-varying ion signals meets a selection criterion, processor 530 instructs mass spectrometer 520 to perform a dependent mass spectrometry scan of the separating sample mixture for a precursor ion of the known compound at the time interval. In other words, the identifying matching signals must meet a combined level or must individually reach a predetermined value for that signal in order to trigger a dependent scan.

In one exemplary embodiment, the selection criterion includes a minimum signal intensity that each of the two or more time-varying ion signals must exceed at the time interval.

In another exemplary embodiment, the selection criterion includes a minimum rate of increase in signal intensity that each of the two or more time-varying ion signals must exceed at the time interval.

In another exemplary embodiment, the selection criterion includes a minimum combined signal intensity that a sum of the intensities each of the two or more time-varying ion signals must exceed at the time interval.

In another exemplary embodiment, the selection criterion comprises a nonzero intensity count for each of the two or more time-varying ion signals at the time interval.

Mass Spectrometry Method

Figure 6:
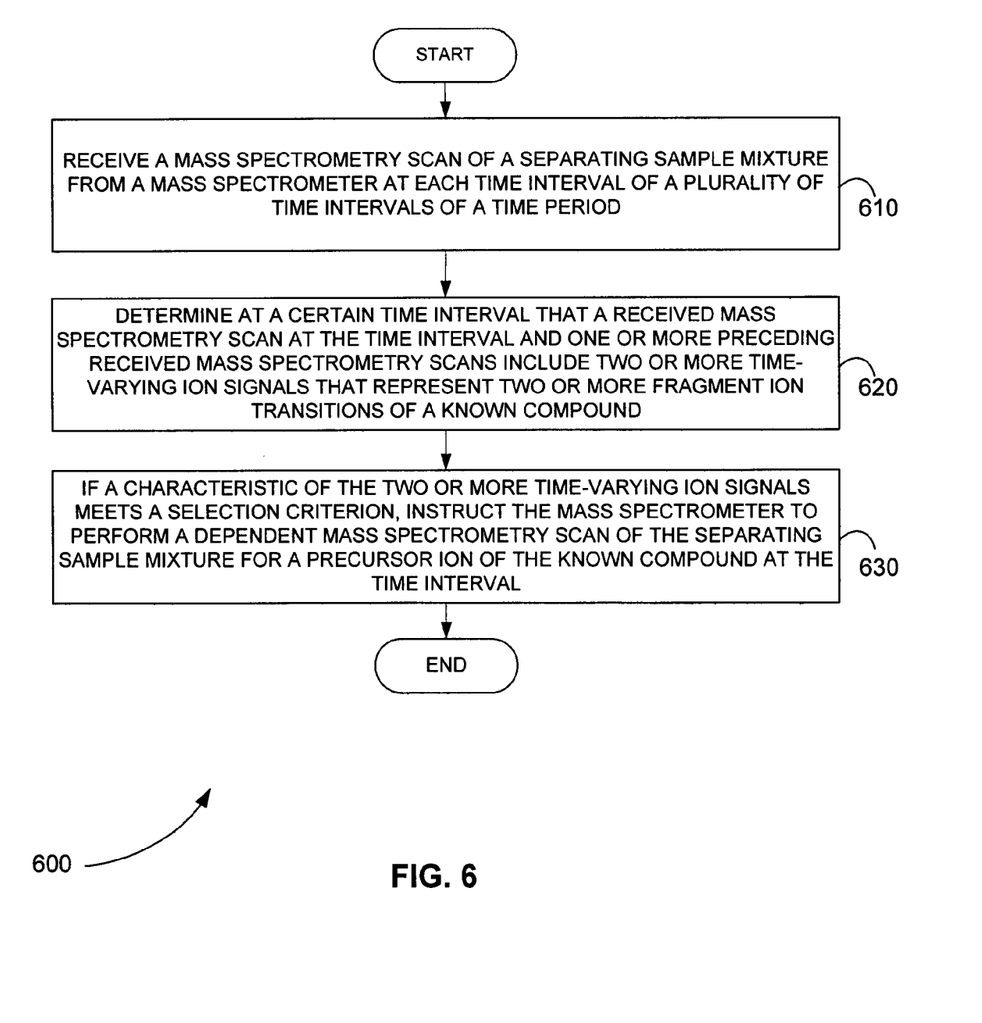
FIG. 6 is an exemplary flowchart showing a method for triggering an information dependent mass spectrometry scan in real time, in accordance with various embodiments.

FIG. 6 is an exemplary flowchart showing a method 600 for triggering an information dependent mass spectrometry scan in real time, in accordance with various embodiments.

In step 610 of method 600, a mass spectrometry scan of a separating sample mixture is received from a mass spectrometer at each time interval of a plurality of time intervals of a time period. The mass spectrometer receives the separating sample mixture from a separation device.

In step 620, it is determined at a certain time interval that a received mass spectrometry scan at the time interval and one or more preceding received mass spectrometry scans include two or more time-varying ion signals that represent two or more fragment ion transitions of a known compound.

In step 630, if a characteristic of the two or more time-varying ion signals meets a selection criterion, the mass spectrometer is instructed to perform a dependent mass spectrometry scan of the separating sample mixture for a precursor ion of the known compound at the time interval.

Mass Spectrometry Computer Program Product

In various embodiments, a computer program product includes a non-transitory and tangible computer-readable storage medium whose contents include a program with instructions being executed on a processor so as to perform a method for triggering an information dependent mass spectrometry scan in real time. This method is performed by a system that includes one or more distinct software modules.

Figure 7:
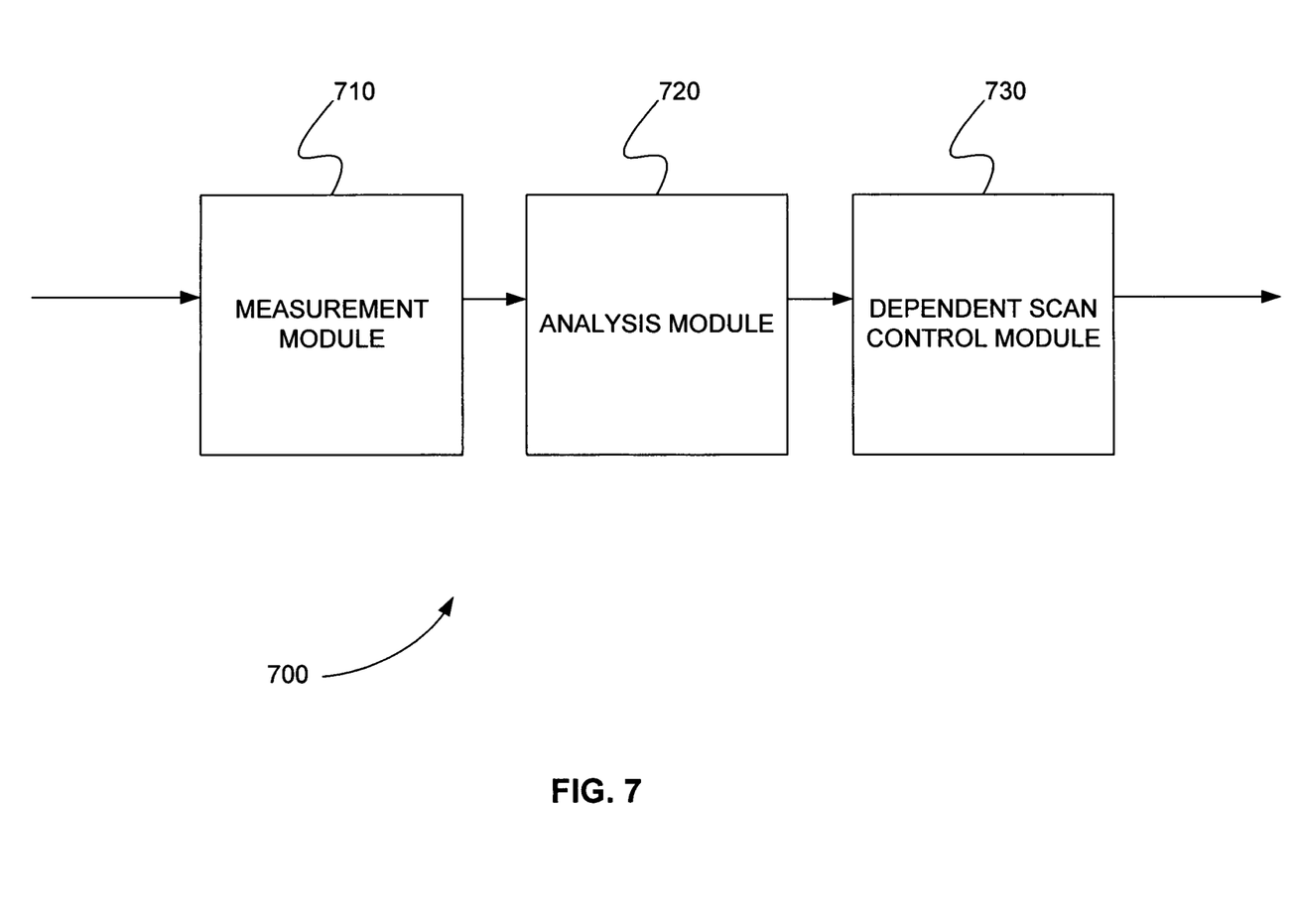
FIG. 7 is a schematic diagram of a system that includes one or more distinct software modules that performs a method for triggering an information dependent mass spectrometry scan in real time, in accordance with various embodiments.

FIG. 7 is a schematic diagram of a system 700 that includes one or more distinct software modules that perform a method for triggering an information dependent mass spectrometry scan in real time, in accordance with various embodiments. System 700 includes measurement module 710, analysis module 720 and dependent scan control module 730.

Measurement module 710 receives a mass spectrometry scan of a separating sample mixture from a mass spectrometer at each time interval of a plurality of time intervals of a time period. The mass spectrometer receives the separating sample mixture from a separation device.

Analysis module 720 determines at a certain time interval that a received mass spectrometry scan at the time interval and one or more preceding received mass spectrometry scans include two or more time-varying ion signals that represent two or more fragment ion transitions of a known compound.

Dependent scan control module 730 instructs the mass spectrometer to perform a dependent mass spectrometry scan of the separating sample mixture for a precursor ion of the known compound at the time interval, if a characteristic of the two or more time-varying ion signals meets a selection criterion.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for triggering an information dependent mass spectrometry scan in real time, comprising:
   a separation device that separates one or more compounds from a sample mixture over a time period;
   a mass spectrometer that performs mass spectrometry scans of a group of two or more multiple reaction monitoring (MRM) transitions of a known precursor ion of a known compound on the separating sample mixture at each time interval of a plurality of time intervals of the time period, wherein each MRM transition of the group of two or more MRM transitions is a transition of the known precursor ion to a different fragment ion; and
   a processor that
      receives from the mass spectrometer at each time interval of the plurality of time intervals a fragment ion intensity for each transition of the group of two or more MRM transitions,
      determines at each time interval of the plurality of time intervals two or more time-varying fragment ion signals that represent fragment ion intensities of the group of two or more MRM transitions at the each time interval and all preceding time intervals for the known compound,
      assigns a single selection criterion to represent the group of two or more MRM transitions by combining each fragment ion intensity of the group of two or more MRM transitions, and
      if each fragment ion intensity of the group of two or more MRM transitions meets the single selection criterion, instructs the mass spectrometer to perform a dependent mass spectrometry scan of the separating sample mixture for the known precursor ion of the known compound at the each time interval.

2. The system of claim 1, wherein the single selection criterion comprises a minimum signal intensity that each of the two or more time-varying fragment ion signals must exceed at the each time interval.

3. The system of claim 1, wherein the single selection criterion comprises a minimum rate of increase in signal intensity that each of the two or more time-varying fragment ion signals must exceed at the each time interval.

4. The system of claim 1, wherein the single selection criterion comprises a minimum combined signal intensity that a sum of the intensities each of the two or more time-varying fragment ion signals must exceed at the each time interval.

5. The system of claim 1, wherein the single selection criterion comprises a nonzero intensity count for each of the two or more time-varying fragment ion signals at the each time interval.

6. A method for triggering an information dependent mass spectrometry scan in real time, comprising:
   receiving from a mass spectrometer a fragment ion intensity for each transition of a group of two or more MRM transitions of a known precursor ion of a known compound measured from mass spectrometry scans of a separating sample mixture at each time interval of a plurality of time intervals of a time period, wherein the mass spectrometer receives the separating sample mixture from a separation device and wherein each MRM transition of the group of two or more MRM transitions is a transition of the known precursor ion to a different fragment ion;
   determining at each time interval of the plurality of time intervals two or more time-varying fragment ion signals that represent fragment ion intensities of the group of two or more MRM transitions at the each time interval and all preceding time intervals for the known compound,
   assigning a single selection criterion to represent the group of two or more MRM transitions by combining each fragment ion intensity of the group of two or more MRM transitions, and
   if each fragment ion intensity of the group of two or more MRM transitions meets the single selection criterion, instructing the mass spectrometer to perform a dependent mass spectrometry scan of the separating sample mixture for the known precursor ion of the known compound at the each time interval.

7. The method of claim 6, wherein the single selection criterion comprises a minimum signal intensity that each of the two or more time-varying fragment ion signals must exceed at the each time interval.

8. The method of claim 6, wherein the single selection criterion comprises a minimum rate of increase in signal intensity that each of the two or more time-varying fragment ion signals must exceed at the each time interval.

9. The method of claim 6, wherein the single selection criterion comprises a minimum combined signal intensity that a sum of the intensities each of the two or more time-varying fragment ion signals must exceed at the each time interval.

10. The method of claim 6, wherein the single selection criterion comprises a nonzero intensity count for each of the two or more time-varying fragment ion signals at the each time interval.

11. A computer program product, comprising a non-transitory and tangible computer-readable storage medium whose contents include a program with instructions being executed on a processor so as to perform a method for triggering an information dependent mass spectrometry scan in real time, the method comprising:
   providing a system, wherein the system comprises one or more distinct software modules, and wherein the distinct software modules comprise a measurement module, an analysis module, and a dependent scan control module;
   receiving from a mass spectrometer a fragment ion intensity for each transition of a group of two or more MRM transitions of a known precursor ion of a known compound measured from mass spectrometry scans of a separating sample mixture at each time interval of a plurality of time intervals of a time period using the measurement module, wherein the mass spectrometer receives the separating sample mixture from a separation device and wherein each MRM transition of the group of two or more MRM transitions is a transition of the known precursor ion to a different fragment ion;
   determining at each time interval of the plurality of time intervals two or more time-varying fragment ion signals that represent fragment ion intensities of the group of two or more MRM transitions at the each time interval and all preceding time intervals for the known compound using the analysis module, assigning a single selection criterion to represent the group of two or more MRM transitions by combining each fragment ion intensity of the group of two or more MRM transitions, and if each fragment ion intensity of the group of two or more MRM transitions meets the single selection criterion, instructing the mass spectrometer to perform a dependent mass spectrometry scan of the separating sample mixture for the known precursor ion of the known compound at the each time interval using the dependent scan control module.

12. The computer program product of claim 11, wherein the single selection criterion comprises a minimum signal intensity that each of the two or more time-varying fragment ion signals must exceed at the each time interval.

13. The computer program product of claim 11, wherein the single selection criterion comprises a minimum rate of increase in signal intensity that each of the two or more time-varying fragment ion signals must exceed at the each time interval.

14. The computer program product of claim 11, wherein the single selection criterion comprises a minimum combined signal intensity that a sum of the intensities each of the two or more time-varying fragment ion signals must exceed at the each time interval.

15. The computer program product of claim 11, wherein the single selection criterion comprises a nonzero intensity count for each of the two or more time-varying fragment ion signals at the each time interval.

16. The system of claim 1, wherein the single selection criterion comprises a minimum signal intensity that an average of each of the two or more time-varying fragment ion signals must exceed at the each time interval.

17. The method of claim 6, wherein the single selection criterion comprises a minimum signal intensity that an average of each of the two or more time-varying fragment ion signals must exceed at the each time interval.

18. The computer program product of claim 11, wherein the single selection criterion comprises a minimum signal intensity that an average of each of the two or more time-varying fragment ion signals must exceed at the each time interval.

19. The system of claim 1, wherein the single selection criterion comprises a minimum rate of increase in signal intensity that a first derivative of each of the two or more time-varying fragment ion signals must exceed at the each time interval.

20. The method of claim 6, wherein the single selection criterion comprises a minimum rate of increase in signal intensity that a first derivative of each of the two or more time-varying fragment ion signals must exceed at the each time interval.

* * * * *